United States Patent [19]

Quaid

[11] Patent Number: 4,889,744
[45] Date of Patent: Dec. 26, 1989

[54] METHOD FOR MAKING OPEN-CELL, SILICONE-ELASTOMER MEDICAL IMPLANT

[75] Inventor: Joel Quaid, Santa Barbara, Calif.

[73] Assignee: Medical Products Development Inc., Santa Barbara, Calif.

[21] Appl. No.: 189,195

[22] Filed: May 2, 1988

Related U.S. Application Data

[62] Division of Ser. No. 927,272, Nov. 4, 1986.

[51] Int. Cl.$^4$ .............................................. A01N 1/02
[52] U.S. Cl. ............................... 427/2; 128/DIG. 21; 623/8; 427/205
[58] Field of Search ............... 128/DIG. 21, 1 R, 155, 128/156; 623/1, 2, 8, 12, 13, 16; 427/2, 205

[56] References Cited

U.S. PATENT DOCUMENTS

| | | | |
|---|---|---|---|
| 4,576,608 | 3/1986 | Homsy | 264/127 |
| 4,648,880 | 3/1987 | Brauman | 623/8 |

*Primary Examiner*—Michael Lusignan
*Attorney, Agent, or Firm*—Michael G. Petit

[57] ABSTRACT

A medical implant with an external surface layer of silicone elastomer and having an open-cell structure is made by applying solid particles to the external surface layer of the implant before it is cured, curing the external surface layer with the solid particles embedded therein and then dissolving the solid particles with a solvent that does not dissolve the silicone elastomer. An implant having such an external surface layer is expected to help prevent capsular contraction, to help prevent scar formation, and to help in anchoring the implant within the body.

16 Claims, 4 Drawing Sheets

METHOD FOR MAKING OPEN-CELL, SILICONE-ELASTOMER MEDICAL IMPLANT

FIELD OF THE INVENTION

The present invention is directed to medical devices suitable for implantation and a method for making the devices. More particularly it is directed to silicone-elastomer prostheses having an open-cell texture at the outer surface and a method for making such a prostheses using soluble solid particles.

BACKGROUND OF THE INVENTION

To be suitable for implantation within the human body, a prosthesis should be made of a material that is not physically or chemically degraded or altered by contact with body fluids, that is not toxic or allergenic to human tissue and that will not excite an inflammatory or foreign body reaction. Over the years, silicone elastomers have been found to be the materials best suited for implantation within the human body, because they come the closest to realizing the above-stated requirements. For this reason, silicone elastomers have been widely used for coating cardiac pacemakers, for making implanted catheters (Irving, Hall & Rickham, *Tissue Reaction to Pure and Impregnated Silastic*, Journal of Pediatric Surgery, Vol. 6, No. 6 at 724 (December 1971)), and for making mammary prostheses. The use of silicone elastomers in the manufacture of mammary prostheses has been especially extensive.

However, despite the relative inertness of silicone elastomers, they may still provoke an inflammatory or foreign body reaction in some patients to varying degrees. When a foreign substance enters human tissues, the immediate and natural reaction of the tissues surrounding the foreign substance is to render it harmless to the rest of the body. Small foreign bodies can be disposed of by phagocytosis, but large and inert foreign bodies are encapsulated in a sheath of fibrous tissue to isolate them from surrounding tissues. Encapsulation is a defensive mechanism that occurs through a process similar to the formation of scar tissue in the healing of a wound or surgical incision. A fibrous tissue capsule will form around and completely enclose an implanted prosthesis in an intimate fashion, conforming to its respective shapes and curvatures.

Capsule formation is not a problem for the patient unless the capsule begins to contract. With an implanted mammary prosthesis, the contracture of the capsule around the prosthesis causes it to be compressed tightly and feel very hard and rigid. Ultimately, the contracted capsule assumes a nearly spherical shape. Capsular contracture causes discomfort and embarrassment to the patients who experience it and is a serious condition both from medical and aesthetic viewpoints. One way to remedy capsular contracture is to surgically remove the contracted capsule and implant and then insert either the same or another implant, a procedure called surgical capsulotomy or capsulectomy. Alternatively, some doctors use closed capsulotomy, a method wherein force is applied to break the capsule in situ. Of course, capsular contracture can still recur.

The problem of capsular contracture is very complex and the reasons why it occurs are not yet fully understood. Nonetheless, several different approaches to avoiding capsular contraction have been investigated. One of the most popular approaches followed today involves the use of steroids. Steroids are known to possess anti-inflammatory and anti-fibrinogenic properties and have been observed to cause a decrease in the relative hardness of breasts implanted with mammary prostheses. However, the use of steroids can result in complications such as tissue atrophy and discoloration of the skin. Accordingly a great deal of controversy surrounds the use of steroids and their relative utility in preventing capsular contracture. Other drugs and techniques have also been suggested, but their utility has not yet been established.

Other approaches to the problem of capsular contracture have focused on the design of the implant. Examples of mammary prostheses designed to prevent or alleviate the effects of capsular contracture are disclosed in U.S. Pat. Nos. 3,189,921; 3,366,975; 3,559,214; 3,600,718; 3,934,274; 4,095,295; 4,298,997; 4,298,998; and 4,428,082. Of these, those receiving the greatest commercial acceptance are made of a flexible, thin-walled container or sac composed of a material impervious to the ingrowth of fibrous tissue, such as a silicone elastomer, to the external surface of which a thin layer of a porous or open-celled material has been adheringly applied (U.S. Pat. Nos. 3,366,975 or 3,559,214). The interior of the sac is filled with an inert material approximating the resiliency of normal mammary tissue, such as a saline solution or a silicone gel.

The porous or open-celled layer is normally composed of a polyether, polyester or polyurethane foam material. Thin layers of this type of material had been applied to the back sides of mammary prostheses so that fibrous tissue could grow into the material and thereby anchor a prosthesis securely to the chest wall (U.S. Pat. No. 3,293,663). However, case studies conducted on mammary prostheses almost completely covered with a thin foam layer indicated that the incidence of capsular contracture was reduced by the use of such prostheses (*Pennisi, Polyurethane-Covered Silicone Gel Mammary prosthesis for Successful Breast Reconstruction*, Aesthetic Plastic Surgery, Vol. 9 at 73 (1985); Ashley, *Further Studies on the Natural-Y Breast Prosthesis*, Plastic and Reconstructive Surgery, Vol. 45, No. 5 at 421 (May 1970)). Although the cause for the reduced incidence is not fully understood, it is believed that the growth of the fibrous tissue into the open-cell layer from many directions prevents the fibrous tissue from contracting in a concerted manner. In other words, the contractions occur in many directions and tend to neutralize each other (Pennisi, supra, at 73).

However, possible problems exist with the use of polyether, polyester or polyurethane foam materials in implants. These materials apparently degrade in the body over a period of time (Brown, Lowry and Smith, *The Kinetics of Hydrolytic Aging of Polyester Urethane Elastomers*, National Bureau of Standards (July 1979); Sherman and Lyons, *The Biological Fate of Implanted Rigid Polyurethane Foam*, Journal of Surgical Research, Vol. 9, No. 3 at 167 (March 1969)). Therefore, the effectiveness of these materials for preventing capsular contracture may disappear as they degrade When capsular contracture does occur and the doctor chooses to surgically remove the implant, it is difficult to ensure that all of the degraded material has been removed. These materials have also been suspected of creating problems with infection and of being carcinogenic.

To avoid the potential problems with existing foam materials and still take advantage of the reduced incidence of capsular contracture attendant with the use of prostheses having a porous or open-celled outer layer, ways have been sought to make a layer of silicone elastomer having an open-cell texture. In U.S. Pat. No. 3,852,832, a mammary prosthesis is disclosed having a fixation means attached to its back side with perforations passing therethrough and ribs projecting therefrom. This fixation means is preferably to be made of a silicone elastomer. Although no method for making such a fixation means is disclosed, it is believed that it would be separately molded. Therefore, the pattern of perforations and ribs would have to be such as to allow removal from a mold. The fixation means must then be attached to the prosthesis.

Ion-beam thruster technology has also been suggested as a way to microtexture breast prostheses (Picha and Siedlak, Ion-Beam Microtexturing of Biomaterials, MD & DI at 39 (April 1984)). However, this would interject an expensive processing step into the manufacture of breast prostheses. Also, it is not clear how the prostheses will be manipulated to achieve microtexturing over the entirety of their contoured surfaces or how effective the regular pattern of a microtextured surface will be at preventing capsular contracture. Other attempts to create an open-celled texture integral to the prosthesis shell through incorporating foaming or blowing agents in the silicone elastomer have not been successful because the surface properties of the silicone elastomers prevent the bubbles formed from connecting to one another or opening at the surface.

Accordingly, a need exists for a silicone elastomer medical implant having an external surface with an open-celled texture. Additionally, a need exists for an efficient and economic method for making such a medical implant.

SUMMARY OF THE INVENTION

In the most general terms, the present invention is directed to a member comprised of silicone elastomer and having an outer layer, at least a portion of which has an open-cell structure at the surface. A method for providing an open-cell structure to a surface of a layer of silicone elastomer is also taught. This method comprises the steps of: applying solid particles to the surface before the layer is fully cured; fully curing the layer; and dissolving the solid particles with a solvent that does not dissolve the silicone elastomer to any appreciable extent. Preferably, the solid particles have a diameter ranging from about 10 microns to about 600 microns so that the resulting cells in the open-cell structure have diameters in this same range. It is also preferable, for the solid particles to be applied so as to achieve a depth within the layer ranging from a portion of one particle diameter to a multiple of many particle diameters so that the resulting interconnected cells extend down from the surface to a depth in this same range. Most preferred is a range from about one to about three times the diameter of the solid particles.

More specifically, the present invention is directed to a medical implant with an external surface layer of silicone elastomer, at least a portion of which has an open-cell structure. Such an implant can be made through a method substantially the same as the three-step method set forth above. Preferably, the solid particles are applied to most of the external surface layer so that most of the external surface has an open-cell structure. The solid particles can also be applied in a number of ways: by sprinkling them over the external surface layer while manipulating the medical implant; by spraying them onto the external surface layer; or by dipping the medical implant into a body of the solid particles.

Even more specifically, the present invention is directed to an improved silicone-elastomer shell for a mammary prostheses, the improvement comprising: at least a portion of the external surface of the mammary prostheses having an open-cell structure. The improved method taught for making a silicone-elastomer shell for a mammary prosthesis is comprised of the steps of: dipping a supported mandrel into a silicone-elastomer dispersion to apply a final layer of silicone elastomer to a shell adhering to the mandrel; allowing the final layer to stabilize after the mandrel is removed from the dispersion; applying solid particles to the final layer; volatilizing the solvent in the final layer; placing the mandrel and the shell with the final layer into an oven maintained at an elevated temperature for a period of time; dissolving the solid particles with a solvent that does not dissolve the silicone elastomer to any appreciable extent; and evaporating any excess solvent remaining on the shell.

DETAILED DESCRIPTION OF THE PREFERRED EMBODIMENT

The preferred embodiment of the present invention will primarily be described in the context of a mammary prosthesis because the present invention is expected to help solve the capsular contraction problem that is particularly troublesome in the implantation of mammary prostheses. However, the present invention should not be considered as limited to such a prosthesis. Instead, the teachings of the present invention should prove to be advantageous wherever capsular contraction can damage a medical implant or cause discomfort to the patient and/or wherever a medical implant is to be anchored through the ingrowth of fibrous tissue. The present invention should also prove advantageous in preventing or controlling scar formation during wound healing after many types of plastic surgery. In addition, the present invention should have general application within the field of mammary prostheses, as it can be used with any of a wide variety of mammary prostheses.

Figure 1:
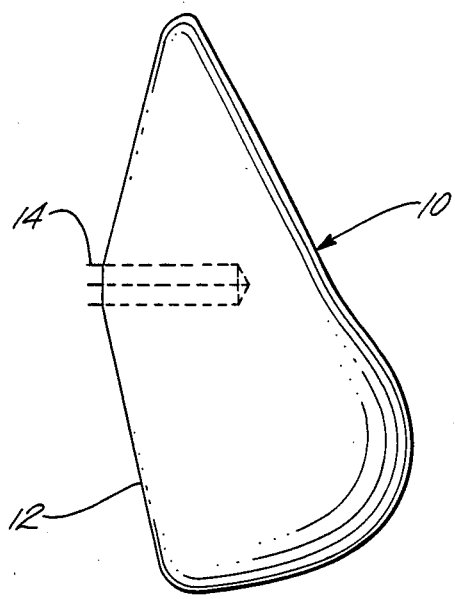
FIG. 1 is a side view of a mandrel used to form a mammary prosthesis according to the present invention.
Figure 2:
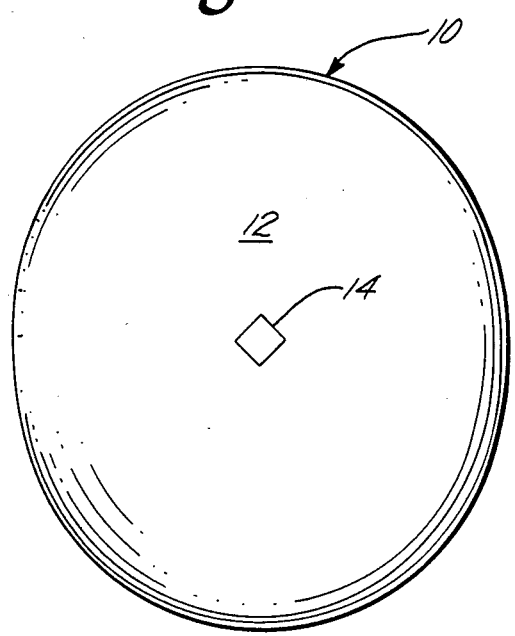
FIG. 2 is a rear view of the mandrel of FIG. 1.

With reference to FIG. 1, a mandrel 10 has an external configuration corresponding to that of the mammary prosthesis to be formed by it. A rear face 12 of the mandrel has a support member 14 embedded therein and extending outward therefrom. As shown in FIG. 2 the support member enters the mandrel at the center of rear face 12. Mandrels of this type are standard in the field. They are typically made of Delrin, aluminum, stainless steel or plastics, such as teflon/nylon combinations or high density polyethylene or polyester resin. The primary consideration is that the material be inert to the solvents and process heat used in the manufacturing process.

To begin the manufacture of a mammary prosthesis, the mandrel is dipped into a silicone rubber dispersion. Many such dispersions are used in the field. Basically they contain a silicone elastomer and a solvent. The silicone elastomer is typically polydimethylsiloxane, polydiphenylsiloxane or some combination of these two. Typical solvents include xylene or trichloromethane. Different manufacturers vary the type and amount of the ingredients in the dispersion, the viscosity of the dispersion and the solid content of the dispersion. Nonetheless, the present invention is expected to be adaptable to have utility with a wide variety of silicone rubber dispersions.

The mandrel is lowered into the dispersion while being supported by support member 14 until the mandrel is completely submerged. The mandrel is then raised out of the dispersion with a thin coating of the material adhering thereto. The solvent in this thin coating is volatilized or caused to evaporate. Normally this is accomplished by flowing air over the coated mandrel at a controlled temperature and humidity. Different manufacturers use various quantities, velocities or directions of air flow and set the temperature and humidity of the air at different values. However, the desired result, driving off the solvent, remains the same. It is also common for prostheses manufacturers to repeat this dip and volatilize procedure a number of times so that a number of layers are built up on the mandrel to reach a desired shell thickness.

It is with the application of the final layer of silicone elastomer, that the present invention departs from the existing procedures for forming prostheses. After the mandrel is raised out of the dispersion with what is to be the final layer adhering thereto, this layer is allowed to stabilize. That is, it is held until the final coating no longer flows freely. This occurs as some of the solvent evaporates from the final coating, raising its viscosity. Once -the layer has stabilized, granulated solid particles are applied evenly over the entire surface. Currently the solid particles are applied manually by sprinkling them over the surface while the mandrel is manipulated. However, it is envisioned that a machine operating like a bead blaster or sand blaster could be used to deliver a steady stream of solid particles at an adequate velocity to the coating on the mandrel. Alternatively, it is envisioned that adequate methods of solid particle application can be developed based on machines that pour the solid particles or based on dipping the coated mandrel into a body of the solid particles or exposing it to a suspension of the solid particles. It is to be understood that the present invention is not intended to be restricted to any one particular method of applying particles.

This final layer, with the solid particles embedded therein, is then allowed to volatilize. After volatilization, the entire silicone elastomer shell structure is vulcanized in an oven at elevated temperatures. The temperature of the oven is preferably kept between about 200° F. and about 350° F. for a vulcanization time preferably between about 20 minutes and about 1 hour, 40 minutes. Upon removal from the oven, the mandrel/shell assembly is placed in a solvent for the solid particles and the solid particles allowed to dissolve. When the solid particles have dissolved, the assembly is removed from the solvent and the solvent evaporated. The shell can then be stripped from the mandrel. At this point, it is preferable to place the shell in a solvent for the solid particles and gently agitate it to ensure dissolution of all the solid particles. When the shell is removed from the solvent, the solvent is evaporated.

Figure 3:
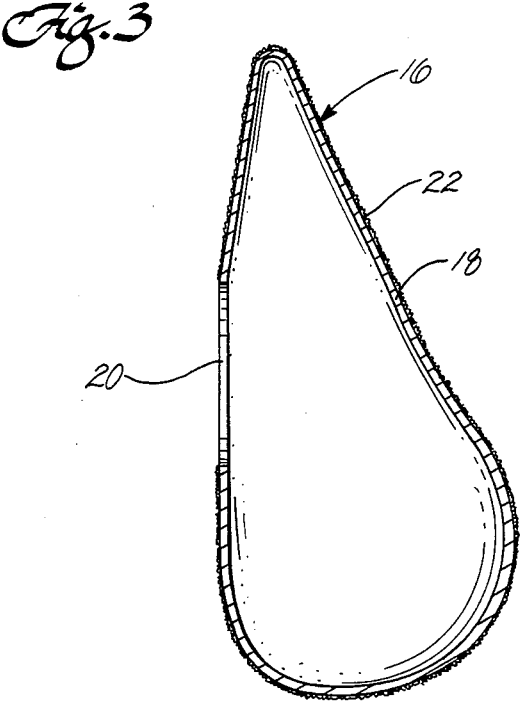
FIG. 3 is a sectioned side view of the shell of a mammary prosthesis according to the present invention.
Figure 4:
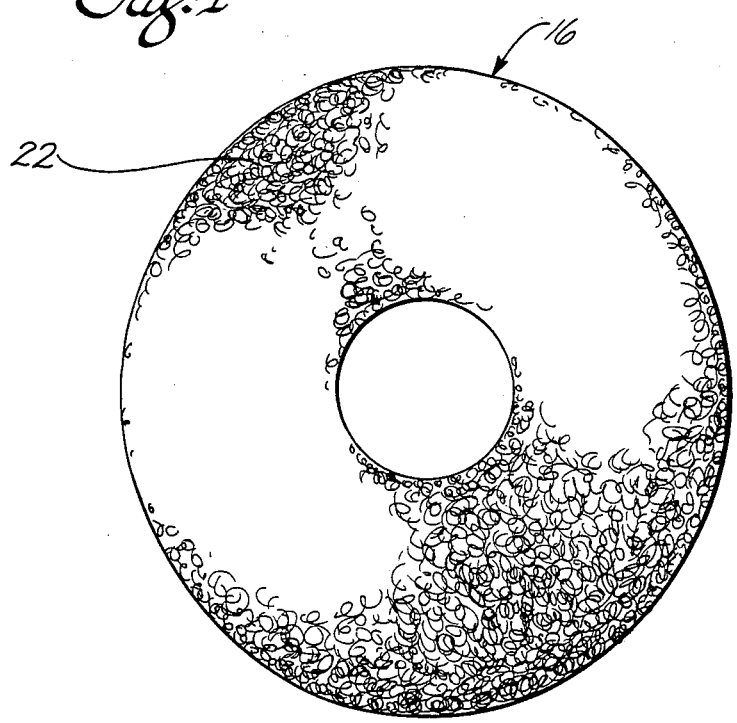
FIG. 4 is a rear view of the shell of a mammary prosthesis of FIG. 3.
Figure 5:
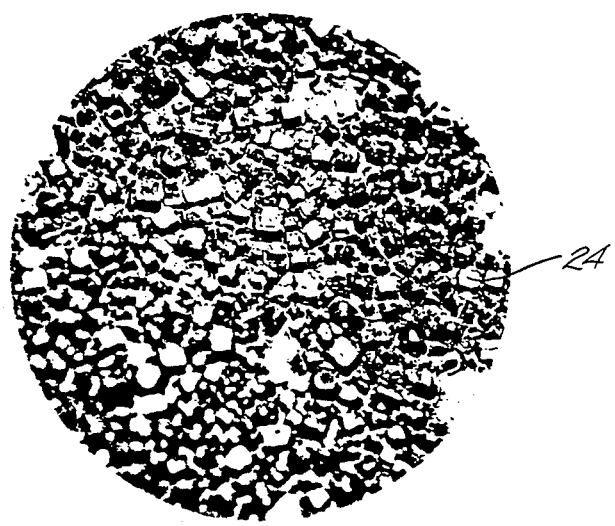
FIG. 5 is a magnified view of the external surface of the shell of a mammary prosthesis containing soluble solid particles.
Figure 6:
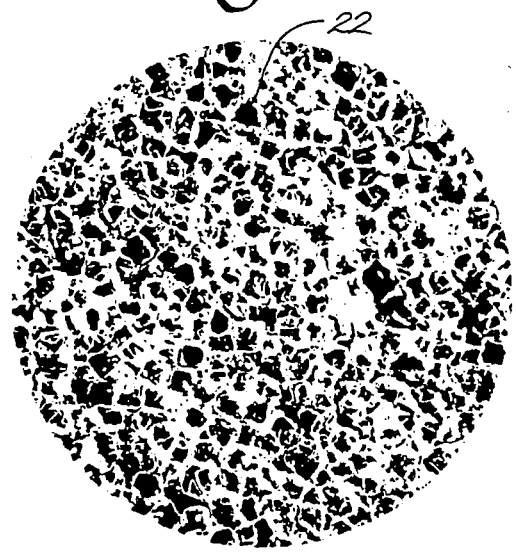
FIG. 6 is a magnified view of the external surface of the shell of a mammary prosthesis showing the open-cell structure remaining after dissolution of the solid particles.

The process described above produces a shell 16 like that shown in FIGS. 3 and 4. The shell has a thin outer wall 18 made of silicone elastomer with an opening 20 therein at the point where support member 14 entered mandrel 12. In addition, the outer surface of the shell is covered with open cells 22 where solid particles 24 used to be before being dissolved. FIGS. 5 and 6 provide magnified views of the process whereby these open cells are formed in the surface of the shell. In FIG. 5, solid particles 24 are shown embedded across the surface of the shell. In FIG. 6, the solid particles have been dissolved, leaving behind open spaces in the surface of the shell. When applied, some of the solid particles are partially exposed so that they can be acted upon by the solvent. These exposed solid particles also provide a way for the solvent to reach those solid particles beneath the surface to dissolve them in turn. The result can be an interconnected structure of cells, some of which are open to the surface, in the outer layer of the shell.

Figure 7:
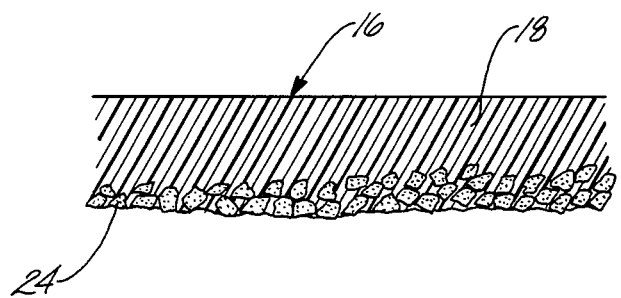
FIG. 7 is a magnified, sectioned side view of the external surface of the shell of a mammary prosthesis containing soluble solid particles.
Figure 8:
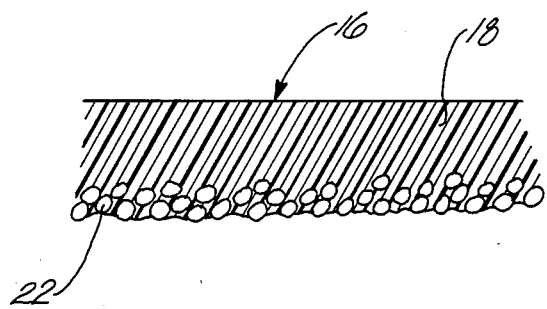
FIG. 8 is a magnified, sectioned side view of the external surface of the shell of a mammary prosthesis showing the open-cell structure remaining after dissolution of the solid particles.

With reference to FIGS. 7 and 8, a magnified side view is provided of the process whereby the open cells are formed in the surface of the shell. In FIG. 7, the solid particles are embedded to a depth of about 0.02 inch in a shell 16 having a thickness of about 0.042 inch. In FIG. 8, the solid particles have been dissolved away to leave behind the open cells.

The object of the solid particle application is to create the type of random, interconnected bubble structure discussed by Dr. R. E. Holmes' research study on tissue ingrowth found in Plastic and Reconstructive Surgery, Vol. 63, at 626–633 (1979). Therefore, the solid particles preferably have diameters ranging from about 10 to about 600 microns. The particles can be applied so as to achieve a depth ranging from a portion of one particle diameter to a multiple of many particle diameters. The particles are preferably embedded in the surface of the shell to a depth of from about one to about three times the diameter of the particles. Penetration of the solid particles depends upon the size of the particles, the thickness of the final uncured layer, the viscosity of the uncured layer and the force with which the particles are applied. These parameters can be controlled to achieve the desired depth of penetration. For example, if the last layer is relatively thick and low is viscosity, less external force will be required on the solid particles to produce an acceptable foam depth.

In choosing a solid, several factors should be evaluated:

(1) the solid should be economically available in the desired particle sizes; (2) the solid should be nontoxic in case some remains in the surface of the prosthesis; and (3) the solid should be readily soluble in a solvent that is economically available, nontoxic and does not dissolve the silicone elastomer. The presently preferred solid is crystalline sodium chloride which is readily available in granulated form. The presently preferred solvent is water, which readily dissolves sodium chloride and does not dissolve silicone rubber. However, the person skilled in the art will understand that a number of solid and solvent pairs could be chosen that would more or less fulfill the above-stated requirements.

After finishing the shell according to the steps described above, the steps required to make a finished mammary prosthesis are again similar to those used by other manufacturers. First, opening 20 is patched with unvulcanized sheeting, usually made of silicone rubber. Then, if the prosthesis is to be filled with silicone gel, this gel is added and cured, the filled prosthesis packaged, and the packaged prosthesis sterilized. If the prosthesis is to be inflated with a saline solution, a one-way valve is assembled and installed, the prosthesis is post cured if required, and the prosthesis is then cleaned, packaged and sterilized. A combination mammary prosthesis can also be made wherein a gel-filled sac is positioned inside the shell to be surrounded by saline solution.

A method has been described for creating an outer layer having an open-cell structure in a silicone elastomer member. More specifically, the method can be applied to create a medical implant with an external surface layer of silicone elastomer having an open-cell structure, to create strips having a textured surface for control of scar formation, or to improve a process for making mammary prostheses. The product made by this method has also been described and is expected to have great utility in preventing capsular contraction, in preventing or controlling scar formation, and in anchoring medical implants.

If capsular contraction does occur with a medical implant made according to the method of the present invention, the doctor is more likely to be able to remove the implant intact. The textured portion of the implant will not degrade so that the doctor can be sure that all of the implant is being removed.

Scar tissue formation in the healing of a wound or surgical incision is also a process involving the growth of fibrous tissue. A visible scar results from this healing process because the fibrous tissue is aligned in one direction. However, it is often aesthetically desirable to prevent scar formation, especially in certain types of plastic surgery. A member having an open-cell structure at the surface can be placed subcutaneously within a healing wound or incision to prevent the fibrous tissue from aligning and thereby prevent scar formation. Such a member can be advantageously made according to the present invention.

It is often important to anchor medical implants against movement. Mammary prostheses are one example of implants that must be anchored. Facial implants are another example of implants that must be anchored. With facial implants it is particularly important that they be anchored securely against movement because of their prominent location. Providing such implants with an open-cell texture according to the present invention is a particularly advantageous way to ensure that they will be anchored securely.

What is claimed is:

1. A method for providing an open-cell structure to a surface of a layer of silicone elastomer, comprising the steps of applying a layer silicone elastomer;
applying solid particles to the surface before the layer is fully cured;
fully curing the layer; and
dissolving the solid particles with a solvent that does not dissolve the silicone elastomer to any appreciable extent.

2. A method according to claim 1, wherein the solid particles have a diameter ranging from about 10 microns to about 600 microns.

3. A method according to claim 2 wherein the solid particles are applied so as to achieve a depth within the layer ranging from about one to about three times the diameters of the solid particles.

4. A method according to claim 1 comprising the additional step of stabilizing the layer of silicone elastomer before applying the solid particles.

5. A method according to claim 1 wherein the fully curing step includes the steps of:
volatilizing the layer of silicone elastomer; and
holding the layer within an oven at an elevated temperature for a period of time.

6. A method according to claim 5 wherein the temperature of the oven is maintained at a temperature between about 200° F. and about 350° F.

7. A method according to claim 5 wherein the period of time the layer is held within the oven is between about 20 minutes and about 100 minutes.

8. A method according to claim 1 wherein the solid particles consist of sodium chloride.

9. A method according to claim 8 wherein the solvent to dissolve the solid particles consists of water.

10. A method for making a medical implant having an external surface layer of silicone elastomer integral therewith, at least a portion of which has an open-cell structure, comprising the steps of applying an external surface layer of silicone elastomer;
applying solid particles to the portion of the external surface layer before the layer is fully cured;
fully curing the external surface layer; and
dissolving the solid particles with a solvent that does not dissolve the silicone elastomer to any appreciable extent.

11. A method according to claim 10 wherein the solid particles are applied to most of the external surface layer.

12. A method according to claim 10 wherein the solid particles are applied by sprinkling them over the external surface layer while manipulating the medical implant.

13. A method according to claim 10 wherein the solid particles are applied by spraying them onto the external surface layer.

14. A method according to claim 10 wherein the solid particles are applied by dipping the medical implant into a body of the solid particles.

15. A method according to claim 10 wherein the solid particles are applied by exposing the medical implant to a suspension of the solid particles.

16. An improved method for making a silicone-elastomer shell for an integral mammary prosthesis, the improvement comprising the steps of:
dipping a supported mandrel into a silicone-elastomer dispersion to apply a final layer of silicone elastomer to a shell adhering to the mandrel;
allowing the final layer to stabilize after the mandrel is removed from the dispersion;
applying solid particles to the final layer;
volatilizing the final layer;
placing the mandrel and the shell into an oven maintained at an elevated temperature for a period of time;
dissolving the solid particles with a solvent that does not dissolve the silicone elastomer to any appreciable extent; and
evaporating any excess solvent remaining on the shell.

* * * * *

REEXAMINATION CERTIFICATE (1943rd)

United States Patent [19]

Quaid

[11] B1 4,889,744

[45] Certificate Issued Mar. 9, 1993

[54] METHOD FOR MAKING OPEN-CELL, SILICONE-ELASTOMER MEDICAL IMPLANT

[75] Inventor: Joel Quaid, Santa Barbara, Calif.

[73] Assignee: Medical Products Development, Inc., Santa Barbara, Calif.

Reexamination Request:
No. 90/002,542, Dec. 13, 1991

Reexamination Certificate for:
Patent No.: 4,889,744
Issued: Dec. 26, 1989
Appl. No.: 189,195
Filed: May 2, 1988

Related U.S. Application Data

[62] Division of Ser. No. 927,272, Nov. 4, 1986, abandoned.

[51] Int. Cl.⁵ .................................................. A61F 2/12
[52] U.S. Cl. .............................. 427/2; 128/DIG. 21; 623/8; 623/901; 427/352; 427/353
[58] Field of Search ................... 128/DIG. 21; 427/2, 427/205, 198, 245, 243, 352, 353; 623/8, 901

[56] References Cited

U.S. PATENT DOCUMENTS

| | | | |
|---|---|---|---|
| 2,688,139 | 9/1954 | Jardon | 3/13 |
| 3,314,420 | 4/1967 | Smith et al. | 128/92 |
| 3,366,975 | 2/1968 | Pangman | 3/36 |
| 3,447,161 | 6/1969 | Weikel | 3/1 |
| 3,462,765 | 8/1969 | Swanson | 3/1 |
| 3,508,554 | 4/1970 | Sheridan | 128/348 |
| 3,605,123 | 9/1971 | Hahn | 3/1 |
| 3,700,380 | 10/1972 | Kitrilakis | 3/1 |
| 4,157,424 | 6/1979 | Boutle | 521/61 |
| 4,242,464 | 12/1980 | Boutle | 521/61 |
| 4,355,426 | 10/1982 | MacGregor | 128/334 X |
| 4,405,360 | 9/1983 | Cardarelli | 71/117 |
| 4,459,252 | 7/1984 | MacGregor | 264/46.9 |
| 4,460,713 | 7/1984 | Lee et al. | 521/122 |
| 4,499,211 | 2/1985 | Walch et al. | 521/145 |
| 4,576,608 | 3/1986 | Homsy | 623/11 |
| 4,643,733 | 2/1987 | Becker | 623/8 |
| 4,648,880 | 3/1987 | Brauman | 623/8 |
| 4,963,150 | 10/1990 | Brauman | 623/8 |

FOREIGN PATENT DOCUMENTS

0159034 10/1985 European Pat. Off. .
1576418 10/1980 United Kingdom .

OTHER PUBLICATIONS

Irving et al, "Tissue Reaction to Pure and Impregnated Silastic", *Journal of Pediatric Surgery*, vol. 6, No. 6, p. 724 (Dec. 1971).

Pennisi, "Polyurethane-Covered Silicone Gel Mammary Prosthesis for Successful Breast Reconstruction", *Aesthetic Plastic Surgery*, vol. 9, p. 73 (1985).

Ashley, "Further Studies on the Natural-Y Breast Prosthesis", *Plastic and Reconstructive Surgery*, vol. 45, No. 5, p. 421 (May 1970).

Brown et al, "The Kinetics of Hydrolytic Aging of Polyester Urethane Elastomers", *National Bureau of Standards, Jul. 1979*.

Sherman et al, "The Biological Fate of Implanted Rigid Polyurethane Foam", *Journal of Surgical Research*, vol. 9, No. 3, p. 167 (Mar. 1969).

Holmes, "Bone Regeneration Within a Coralline Hydroxyapatite Implant", *Plastic & Reconstructive Surgery*, vol. 63, No. 5, pp. 626–633 (May 1979).

Ersek et al, "A New Arteriovenous Shunt Design", *Trans. Ameri. Soc. Artifi. Inter. Orgs.*, vol. XV, Jun. 1989, pp. 267–271.

White et al, "Histopathologic Observations After Short-Term Implantation of Two Porous Elastomers in Dogs", *Biomaterials* 1981, vol. 2 Jul., pp. 171–176.

Salvatore et al, "An Experimental Study of the Influence of Pore Size of Implanted Polyurethane Sponges Upon Subsequent Tissue Formation", *Surgery, Gynecology & Obstetrics*, vol. 112, pp. 464–468 (Apr. 1961).

Wilflingseder et al, "Constrictive Fibrosis Following Silicone Implants in Mammary Augmentation", *Chir. Plastica(Berl.)* 2, pp. 215–229 (1974).

Hipps et al, "Influence of Some Operative and Postoperative Factors on Capsular Contracture Around Breast Prostheses", *Plastic & Reconstructive Surgery*, vol. 61, No. 3, pp. 384–389 (Mar. 1978).

Cairns et al, "Capsular Contracture After Breast Augmentation—A Comparison Between Gel- and Saline-Filled Prostheses", *South Africa Medical Journal*, pp. 951-953 (Jun. 7, 1980).

Untitled paper, Feldman et al, published at Second World Congress on Biomaterials, 10th Annual Meeting at the Society for Biommaterials, Washington, D.C., Apr. 27 May 1, 1984, p. 37.

Feldman, D. et al; *Factors Affecting Soft Tissue Ingrowth into Porous Implants*, Biomaterials Annual Meeting, Apr. 27-May 1, 1984, paper No. 37.

*Primary Examiner*—Shrive' P. Beck
*Attorney, Agent, or Firm*—Christie, Parker & Hale

[57] ABSTRACT

A medical implant with an external surface layer of silicone elastomer and having an open-cell structure is made by applying solid particles to the external surface layer of the implant before it is cured, curing the external surface layer with the solid particles embedded therein and then dissolving the solid particles with a solvent that does not dissolve the silicone elastomer. An implant having such an external surface layer is expected to help prevent capsular contraction, to help prevent scar formation, and to help in anchoring the implant within the body.

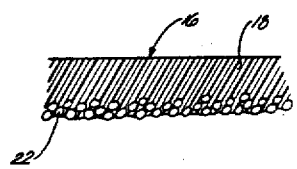

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 2 is cancelled.

Claims 1, 3, 10 and 16 are determined to be patentable as amended.

Claims 4–9 and 11–15 dependent on an amended claim, are determined to be patentable.

New claims 17–23 are added and determined to be patentable.

1. A method for providing an open-cell structure to a surface of a layer of a silicone elastomer *shell of a mammary prosthesis, the method* comprising the steps of [applying a layer silicone elastomer: [;

forming a layer of uncured silicone elastomer having an exposed surface;

forcing a first group of solid particles through the exposed surface and into the layer to a first range of depths where they are completely below the exposed surface of the uncured silicone elastomer;

forcing a second group of solid particles against the exposed surface and into the layer to a second range of depths less than the first so a part of each particle in the second group is not covered by the uncured silicone elastomer, and so particles in the second group contact particles in the first group,

[applying solid particles to the surface before the layer is fully cured;] *wherein the solid particles have a diameter ranging from about 10 microns to about 600 microns;* fully curing the layer *of uncured silicone elastomer in the shell of the mammary prosthesis;* and

[dissolving the solid particles with a solvent that does not dissolve the silicone elastomer to any appreciable extent]

*contacting the exposed surface of cured silicone elastomer with a solvent for the particles, but which does not dissolve the silicone elastomer to any appreciable extent so particles in the second group dissolve and provide a way for the particle solvent to reach and dissolve particles in the first group to form the open-cell structure having an interconnected network of cells, wherein some of the cells open directly to the exposed surface, and other cells communicate with the exposed surface only through cells which open directly to the exposed surface.*

3. A method according to claim [2] *1* wherein the solid particles are applied so as to achieve a depth within the layer ranging from about one to about three times the diameters of the solid particles.

10. A method for making a medical *mammary* implant having an external surface layer of silicone elastomer integral therewith, at least a portion of which has an open-cell structure, *the method* comprising the steps of [applying an external surface layer of silicone elastomer;]:

*forming a layer of uncured silicone elastomer having an exposed surface;*

*forcing a first group of solid particles through the exposed surface and into the layer to a first range of depths where they are completely below the exposed surface of the uncured silicone elastomer;*

*forcing a second group of solid particles against the exposed surface and into the layer to a second range of depths less than the first so a part of each particle in the second group is not covered by the uncured silicone elastomer, and so particles in the second group contact particles in the first group,*

*wherein the solid particles have a diameter ranging from about 10 microns to about 600 microns;*

[applying solid particles to the portion of the external surface layer before the layer is fully cured;]

[fully] curing the [external surface] layer *of the mammary implant;* and

[dissolving the solid particles with a solvent that does not dissolve the silicone elastomer to any appreciable extent]

*contacting the exposed surface of cured silicone elastomer with a solvent for the particles, but which does not dissolve the silicone elastomer to any appreciable extent so particles in the second group dissolve and provide a way for the particle solvent to reach and dissolve particles in the first group to form the open-cell structure having an interconnected network of cells, wherein some of the cells open directly to the exposed surface, and other cells communicate with the exposed surface only through cells which open directly to the exposed surface.*

16. An improved method for making [a] *an integral* silicone-elastomer shell for [an integral] *a* mammary prosthesis, [the improvement comprising] *the shell consisting of a textured silicone elastomer made by* the steps [of] *comprising*:

*dipping a supported mandrel into a silicone-elastomer dispersion, comprising silicone-elastomer and a first solvent, to apply at least one initial layer of silicone elastomer to the mandrel;*

*volatilizing the first solvent from the at least one initial layer;* dipping [a supported] *the* mandrel into [a] *the* silicone-elastomer dispersion to apply a final layer of silicone elastomer to [a shell] *the volatilized at least one initial layer* adhering to the mandrel;

allowing the final layer to stabilize after the mandrel is removed from the dispersion *but not completely volatilize;* applying solid particles to the final layer;

volatilizing *the first solvent from* the final layer;

placing the mandrel and the shell into an oven maintained at an elevated temperature for a period of time *to vulcanize the silicone-elastomer and form the integral shell for a mammary prosthesis;* dissolving the solid particles with a *second* solvent that does not dissolve the silicone elastomer to any appreciable extent; and evaporating any excess *of the second* solvent remaining on the shell.

*17. A method for making a shell for a mammary implant having an external surface layer of silicone elastomer* as a part thereof, the external surface layer consisting of a textured silicone elastomer made by the steps comprising:
dipping a supported mandrel into a silicone-elastomer dispersion, comprising silicone-elastomer and a first solvent, to apply at least one initial layer of silicone elastomer to the mandrel;
volatilizing the first solvent from the at least one initial layer;
dipping the mandrel into the silicone-elastomer dispersion to apply an external surface layer of silicone elastomer to the volatilized at least one initial layer adhering to the mandrel;
allowing the external surface layer to stabilize after the mandrel is removed from the dispersion;
applying solid particles to the external surface layer;
volatilizing the first solvent from the external surface layer;
vulcanizing the layers of silicone elastomer to form an integral shell for a mammary implant;
dissolving the solid particles with a second solvent that does not dissolve the silicone elastomer to any appreciable extent; and
evaporating any excess of the second solvent remaining on the shell.

18. A method according to claim 17 wherein the step of applying solid particles includes the steps of:
forcing a first group of solid particles into the external surface layer to a first range of depths where they are completely below the exposed surface of the silicone elastomer; and
forcing a second group of solid particles into the external surface layer to a second layer of depths less than the first so a part of each particle in the second group is not covered by the silicone elastomer, and so particles in the second group contact particles in the first group.

19. A method according to claim 17 wherein the solid particles are applied by sprinkling them over the external surface layer while manipulating the shell for a mammary implant.

20. A method according to claim 17 wherein the solid particles are applied by spraying them onto the external surface.

21. A method according to claim 17 wherein the solid particles are applied by dipping the shell for a mammary implant into a body of the solid particles.

22. A method according to claim 17 wherein the solid particles are applied by exposing the shell for a mammary implant to a suspension of the solid particles.

23. A method according to claim 17 also including the step of agitating the shell during dissolving of the solid particles.

* * * * *